United States Patent
Lu (12)

(10) Patent No.: US 8,007,478 B2
(45) Date of Patent: Aug. 30, 2011

(54) PORTABLE TYPE HYGIENE WASHER

(76) Inventor: Sung-Seng Lu, Daya Township, Taichung County (TW)

( * ) Notice: Subject to any disclaimer, the term of this patent is extended or adjusted under 35 U.S.C. 154(b) by 0 days.

(21) Appl. No.: 12/149,005

(22) Filed: Apr. 24, 2008

(65) Prior Publication Data

US 2010/0312199 A1 Dec. 9, 2010

(30) Foreign Application Priority Data

Dec. 31, 2007 (TW) .............................. 96222612 U

(51) Int. Cl.
*A61M 31/00* (2006.01)
(52) U.S. Cl. ........................................................ 604/279
(58) Field of Classification Search .................. 604/279, 604/275, 39, 187, 40, 42, 41
See application file for complete search history.

(56) References Cited

U.S. PATENT DOCUMENTS

| 4,200,097 | A | * | 4/1980 | Hobbs et al. .................. 604/213 |
| 4,351,336 | A | * | 9/1982 | Sneider .......................... 604/212 |
| 4,531,659 | A | * | 7/1985 | Wright ........................... 222/190 |
| 4,650,470 | A | * | 3/1987 | Epstein .......................... 604/149 |
| 4,964,852 | A | * | 10/1990 | Dunning et al. ................. 604/75 |
| 5,409,167 | A | * | 4/1995 | Borod ............................ 239/152 |
| 2002/0177534 | A1 | * | 11/2002 | Paul ............................... 510/130 |
| 2003/0220620 | A1 | * | 11/2003 | McMurdo ...................... 604/279 |
| 2004/0068222 | A1 | * | 4/2004 | Brian .............................. 604/65 |
| 2004/0161447 | A1 | * | 8/2004 | Paul ............................... 424/430 |

* cited by examiner

*Primary Examiner* — Kevin C Sirmons
*Assistant Examiner* — Michael J Anderson
(74) *Attorney, Agent, or Firm* — Jackson IP PLLC; Demian K. Jackson

(57) ABSTRACT

A portable type hygiene washer comprises bottle body, fixing cover, adjusting cap, dispense lever and valve device, wherein fixing cover being lockingly combined with bottle opening of bottle body is protrudingly made with a liquid dispense ring and a vent hole; the adjusting cap is centrally made with a liquid dispense hole thereon and is made with a positioning ring flange to be sleevedly combined with liquid dispense ring of the fixing cover; the dispense lever having several nozzle holes at front end thereof is lockingly engaged with the top section of adjusting cap; the valve device comprising a tube piece, a ball and a ball retainer with a ball being contained inside thereof is sleevedly affixed to bottom end of tube piece; as such to allow woman in menstruation to thoroughly cleanse vagina or to wash anal area after toilet use thereby achieving multiple useful results.

6 Claims, 16 Drawing Sheets

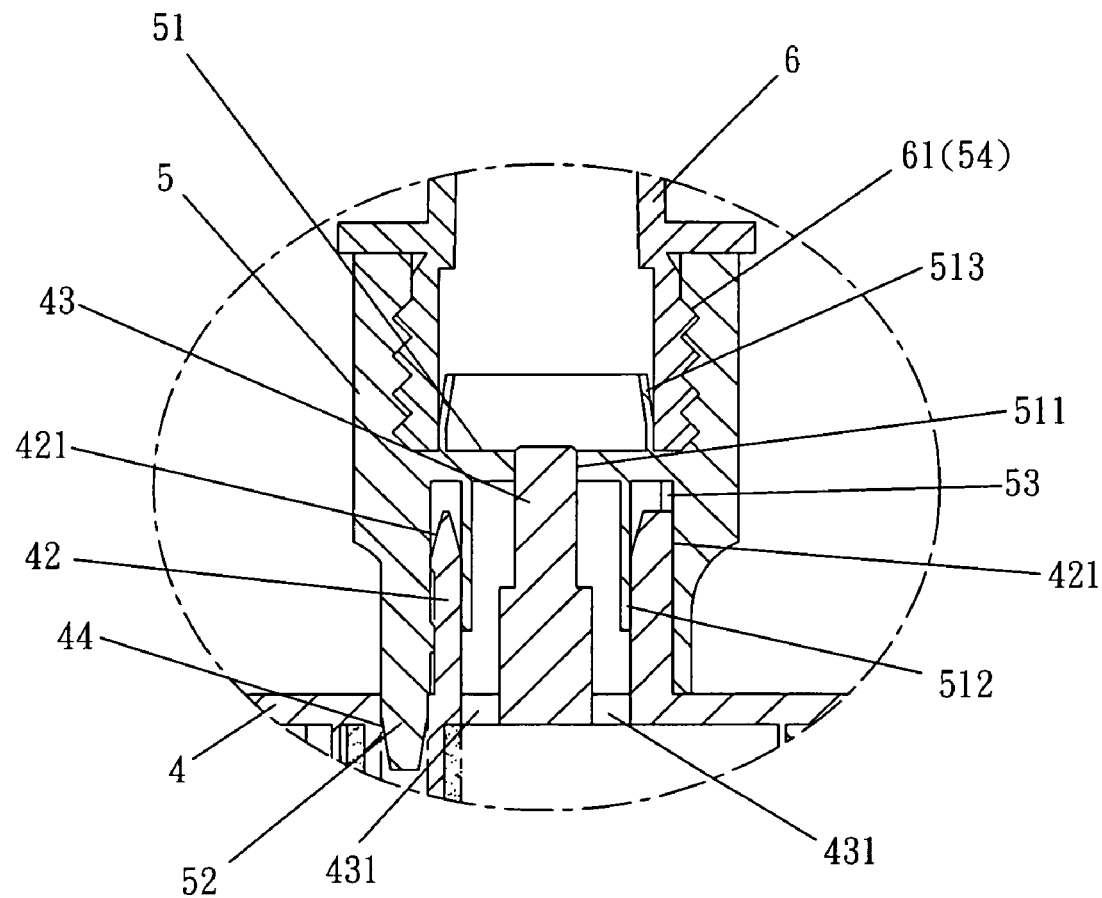
Fig.5-A

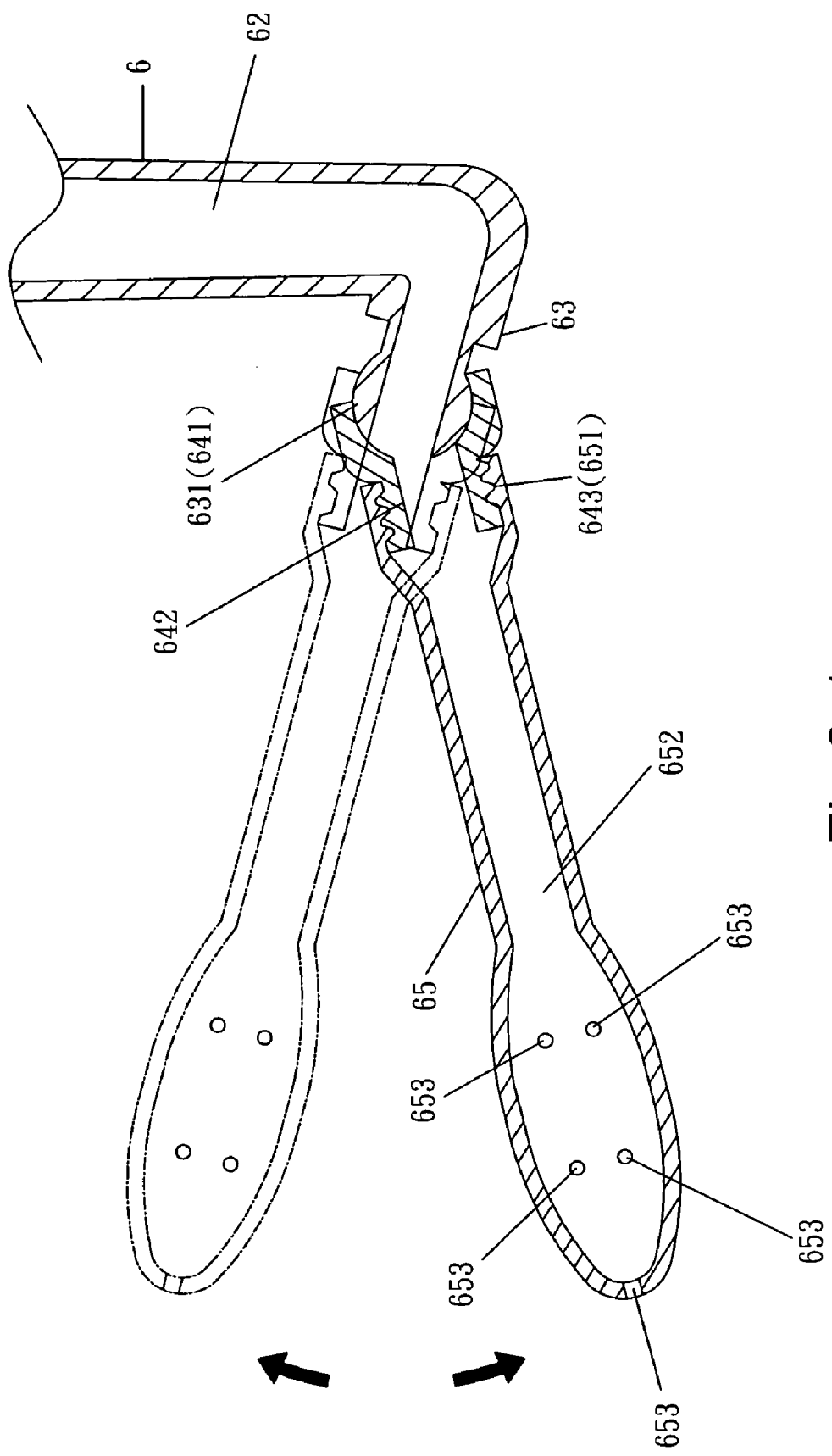
Fig.6-A

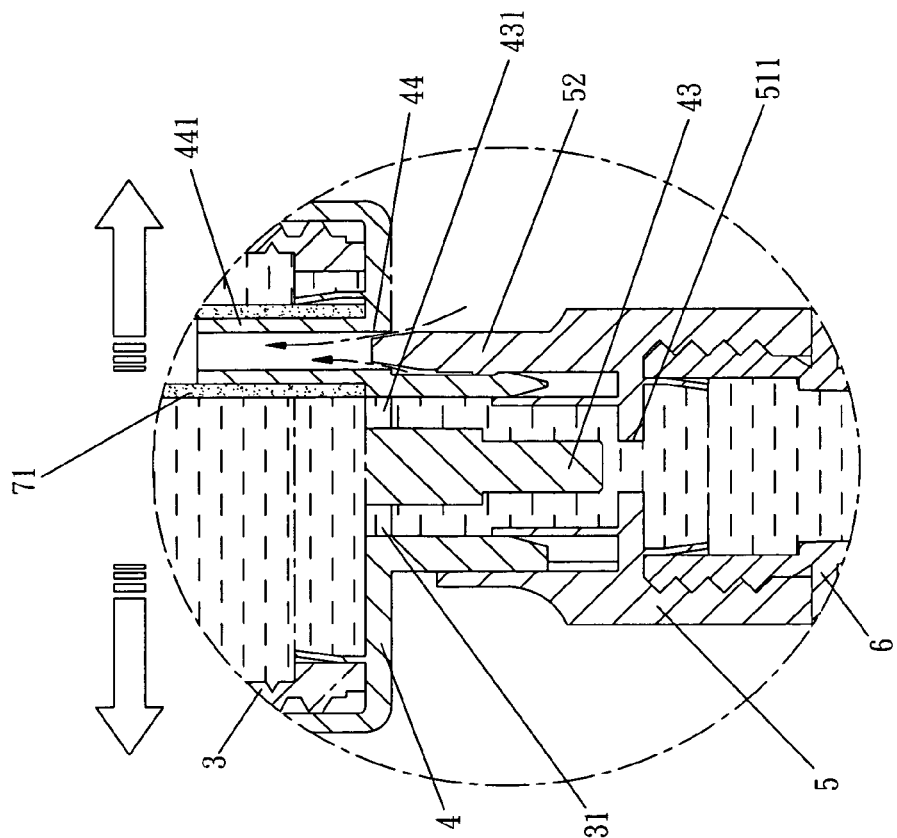
Fig.10-A
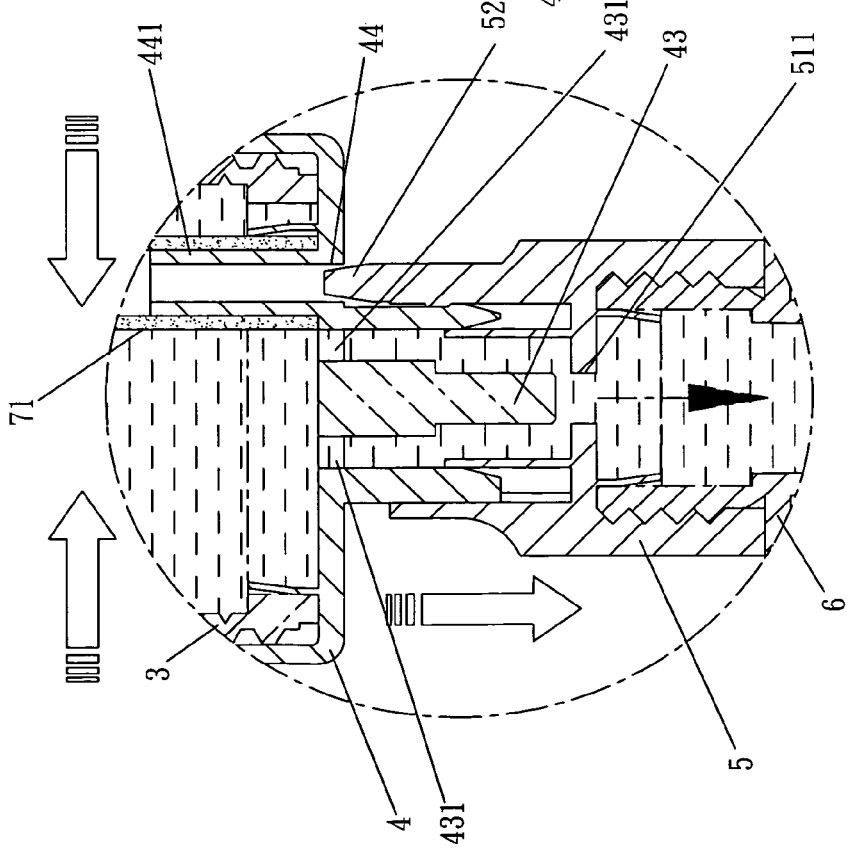
Fig.9-A

PORTABLE TYPE HYGIENE WASHER

BACKGROUND OF THE INVENTION (a) Field of the Invention

The invention is related to a portable type hygiene washer, more particularly to a structure innovation which provides the convenience for women to do thorough cleaning during menstruation and anal cleansing after toilet use.

(b) Description of the Prior Art

As shown in FIG. 1, the portable type hygiene washer 2 currently sold in the market comprises: a bottle body 21 and a spray head 22, wherein bottle body 21 being made of elastic material is internally made to a hollow shape and is centrally made with a inserting hole 211 being interconnected with the interior thereof on top surface thereof, while bottom section 221 of spray head 22 being made with a flow path 222 can be inserted into the inserting hole 211 of bottle body 21.

Through above said structure, for woman in menstruation, cleansing fluid can be filled into bottle body 21 of the hygiene washer 2, whereby spray head 22 is inserted into woman's vagina while pressing bottle body 21 to spray cleansing fluid from the exit of flow path 222 of spray head 22 into vagina thereby achieving the cleaning effect.

For above said structure, as spray head 22 of hygiene washer 2 is straightly inserted in inserting hole 211 on top surface of bottle body 21, woman has to stand up in order to allow spray head 22 to be inserted into her vagina for the cleaning operation to spraying cleansing fluid for wash thereby causing inconvenience; further, as hygiene washer 2 is upwardly opened, hand held bottle body 21 by user make spray head 22 have to be upwardly aligningly inserted into vagina and that raises concerns of soiling solution carrying menstruous blood flowing along surface of spray head 22 and bottle body 21 to stickily moisten the hand thereby causing serious disadvantages of inconvenient and unhygienic operations.

In addition, people after defecation by toilet use usually use toilet papers to wipe clean the anus and normally two or three times are required in order to wipe out the residual feces on the anus to appear cleaner. However, in reality, it is not possible to obtain complete cleaning by wiping with toilet papers. In case of diarrhea, it is more difficult to clean, as the excrement is water like sticky feces, further, if it is forcibly wiped, the anus may be caused to feel pain, especially for persons with hemorrhoid or anus inflammation, they will feel more painful when wiping the anus with toilet papers, therefore other washing devices are expected to improve and overcome said problems.

SUMMARY OF THE INVENTION

The present invention is hence aiming to improve said structures. The main purpose of the present invention is to disclose a portable type hygiene washer comprising bottle body, fixing cover, adjusting cover, dispense lever and valve device; wherein fixing cover being lockingly combined with bottle body is protrudingly made with a liquid dispense ring and a vent hole, the adjusting cap is centrally made with a liquid dispense hole thereon and is externally made with an inserting post for matching with vent hole of fixing cover at peripheral edge of bottom section thereof, is made with a positioning ring flange to be sleevedly combined with liquid dispense ring of the fixing cover; the dispense lever having several nozzle holes at front end thereof is lockingly engaged with the top section of adjusting cap; the valve device comprising a tube piece, a ball and a ball retainer with a ball being contained inside thereof is sleevedly affixed to bottom end of tube piece; as such of its simple structure and convenience of easy carrying on the go to allow woman in menstruation to thoroughly cleanse vagina or to wash anal area after toilet use thereby achieving double useful effects.

BRIEF DESCRIPTION OF THE DRAWINGS

FIG. 5-A is a partially enlarged schematic view of the invented structure.

FIG. 6-A is a partially enlarged cross-sectional view showing the operation of partial structure of the invention (dispense lever portion)

FIG. 9-A is an enlarged cross-sectional schematic view showing partially embodied structure of the invention.

FIG. 10-A is an enlarged cross-sectional schematic view showing partially embodied structure of the invention.

DETAIL DESCRIPTION OF THE PREFERRED EMBODIMENTS

Figure 1:
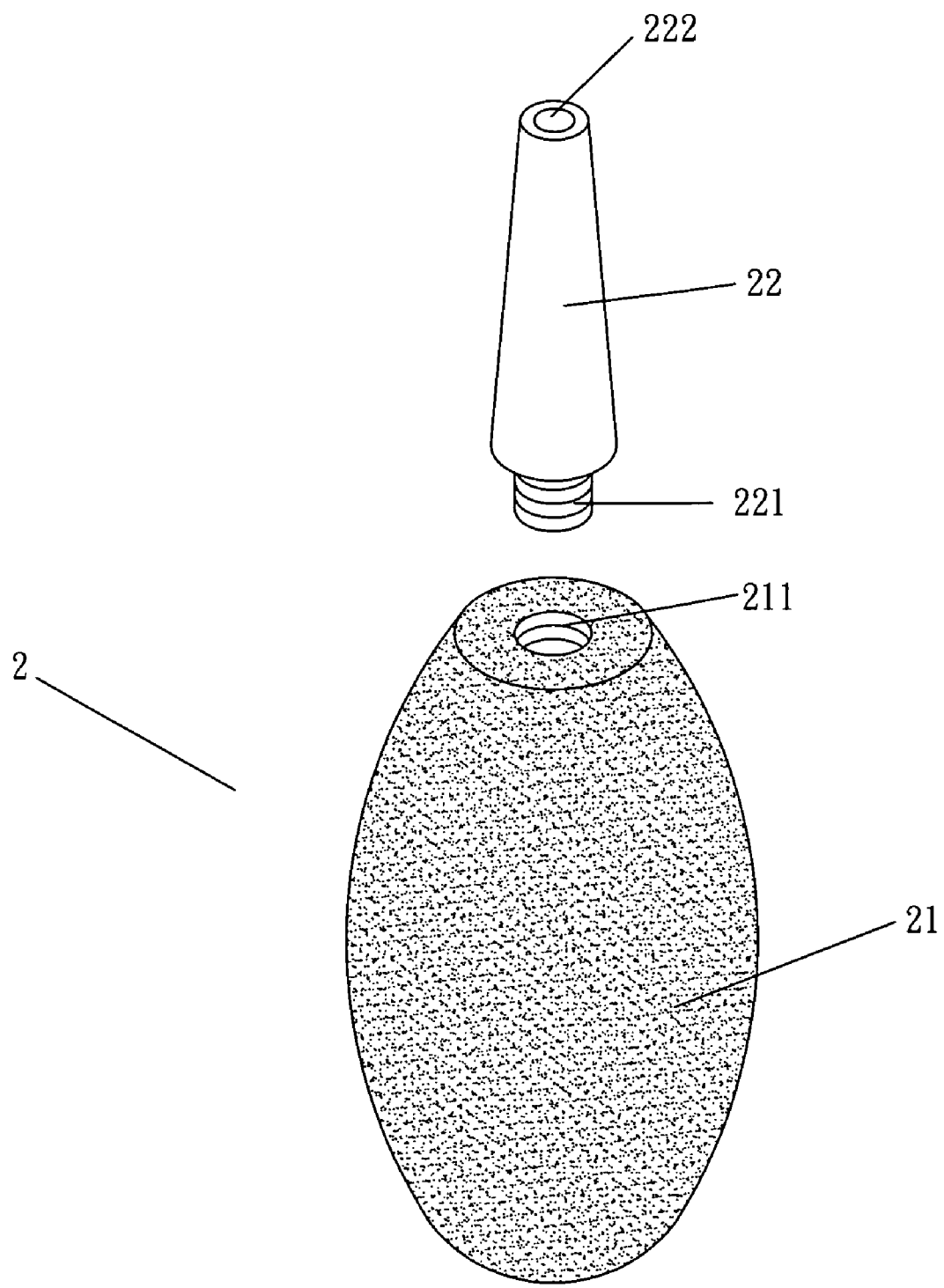
FIG. 1 is a perspective schematic view of the conventional structure.

The portable hygiene washer of the invention as shown in FIG. 2 to FIG. 5-A includes: a bottle body 3 being made of compressible material has a bottle opening 31 being peripherally made with threaded section 311.

A fixing cover 4 being internally made with threaded section 41 being lockingly combined with the top bottle opening 31 of bottle body 3 is protrudingly made with a liquid dispense ring 42, wherein the liquid dispense ring 42 is perpendicularly made with a guide post 421 and is made with an outwardly expanded flange 422 at external ring edge of the top end thereof, the fixing cover 4 is protrudingly centrally made with a column 43 on top surface thereof, the column 43 is peripherally interconnected with the inner peripheral edge of the liquid dispense ring 42 through several linking ribs 431, and the cover 4 is made with a vent hole 44 thereon near to the external peripheral edge of the liquid dispense ring 42, and a positioning tube 441 is protrudingly made at peripheral edge of the vent hole 44 at the bottom surface thereof.

Figure 5:
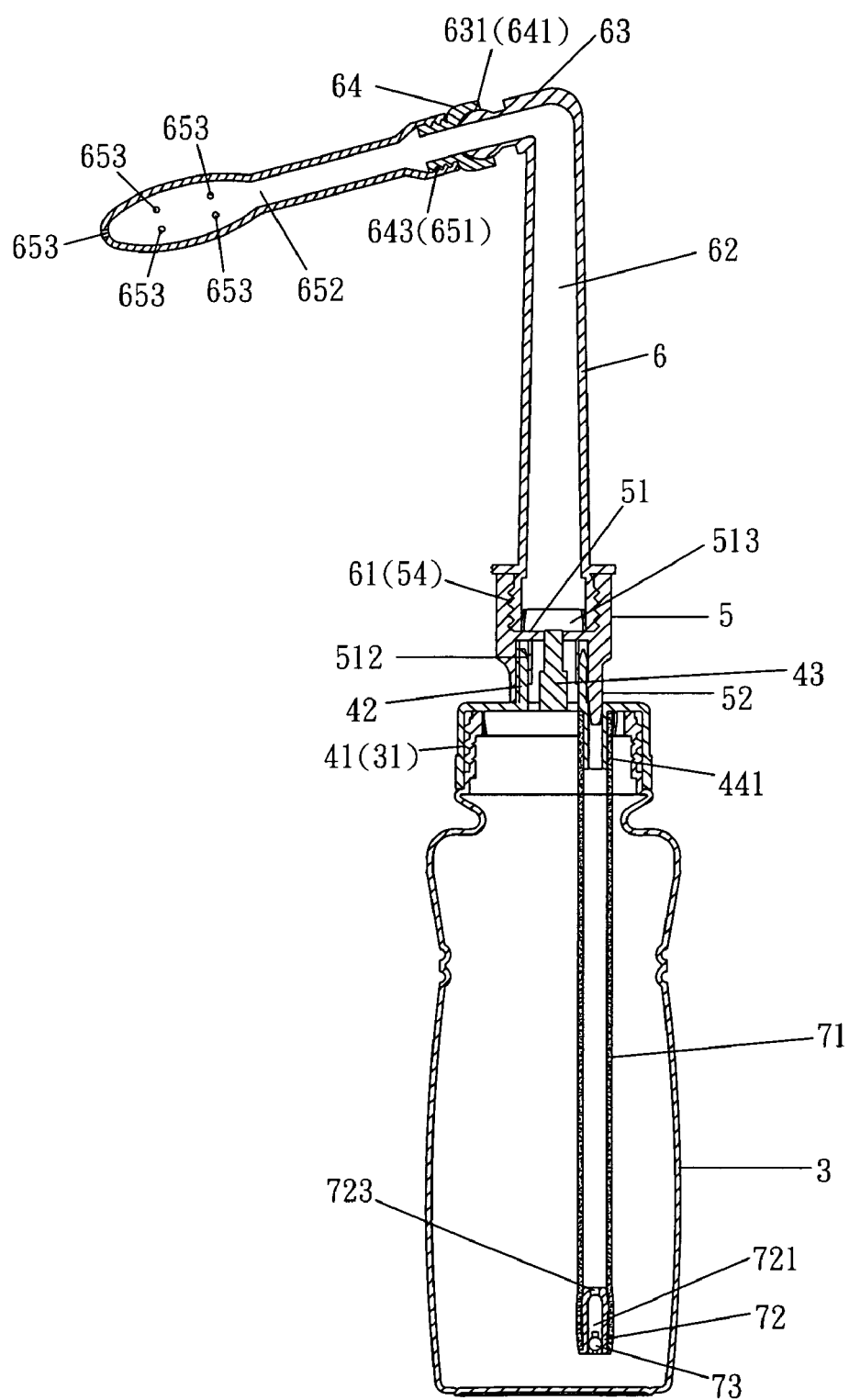
FIG. 5 is a cross-sectional schematic view showing the embodied structure of the invention.
Figure 6:
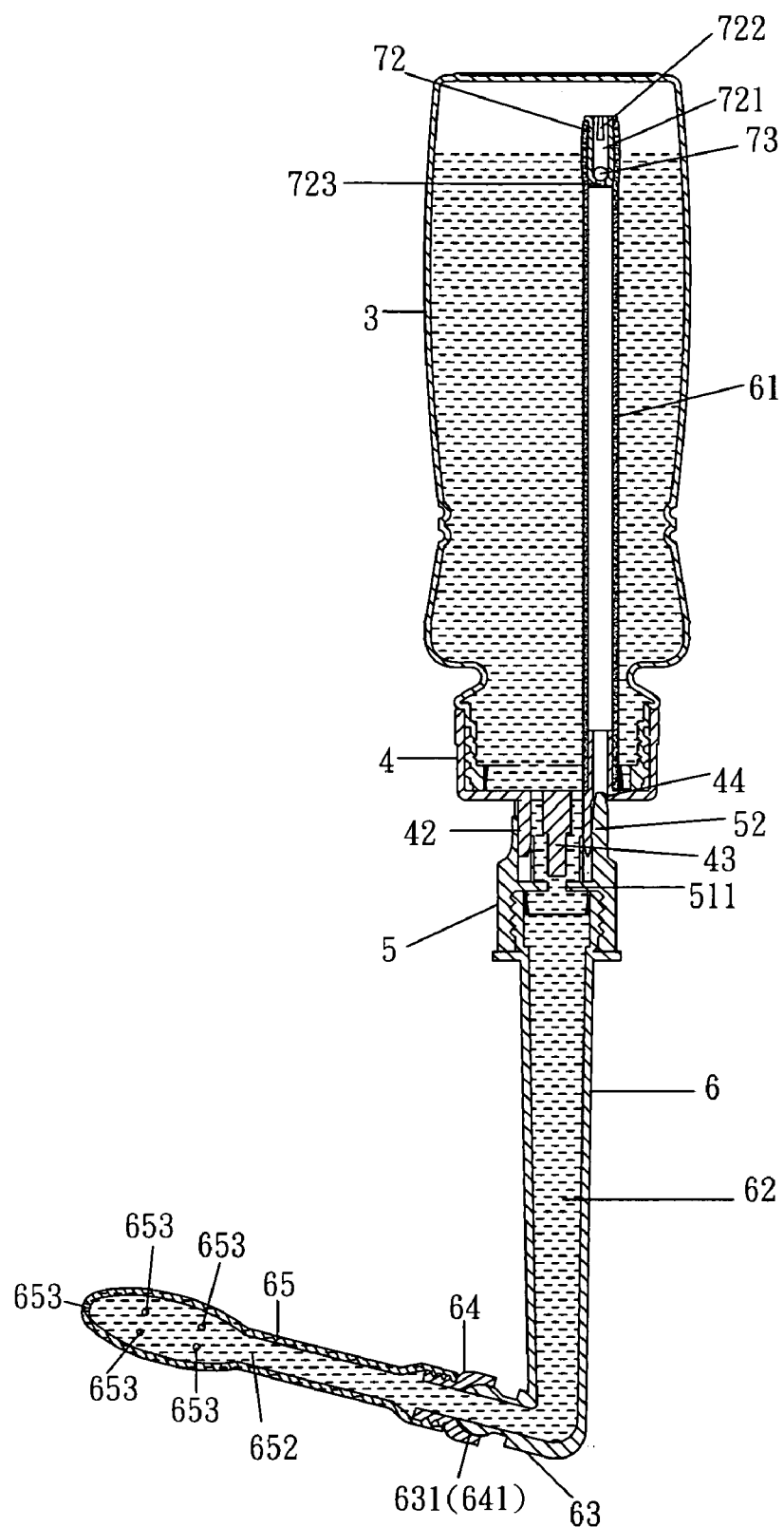
FIG. 6 is a cross-sectional schematic view showing the embodied structure of the invention.
Figure 7:
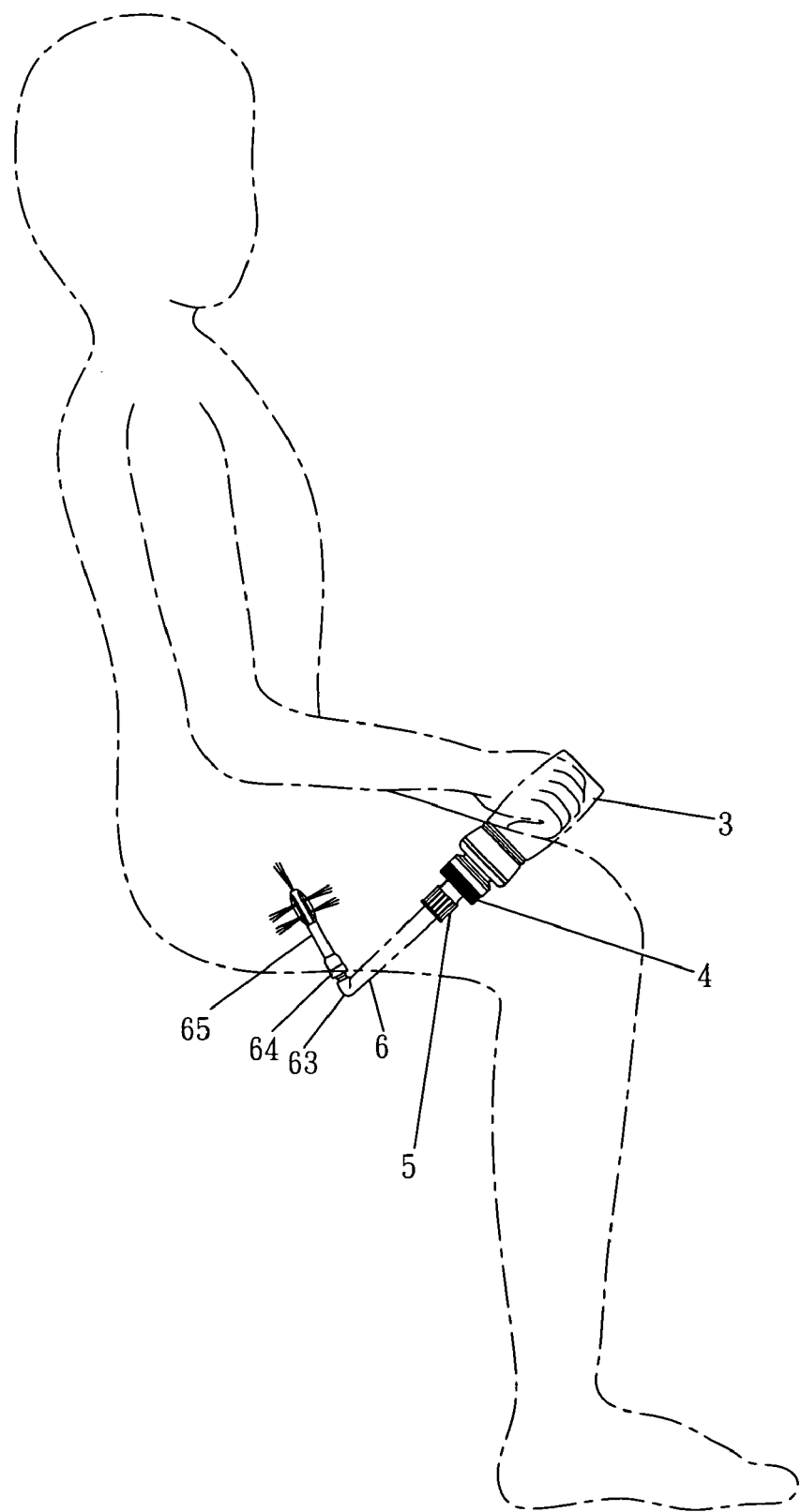
FIG. 7 is a schematic view showing the embodied structure of the invention.
Figure 8:
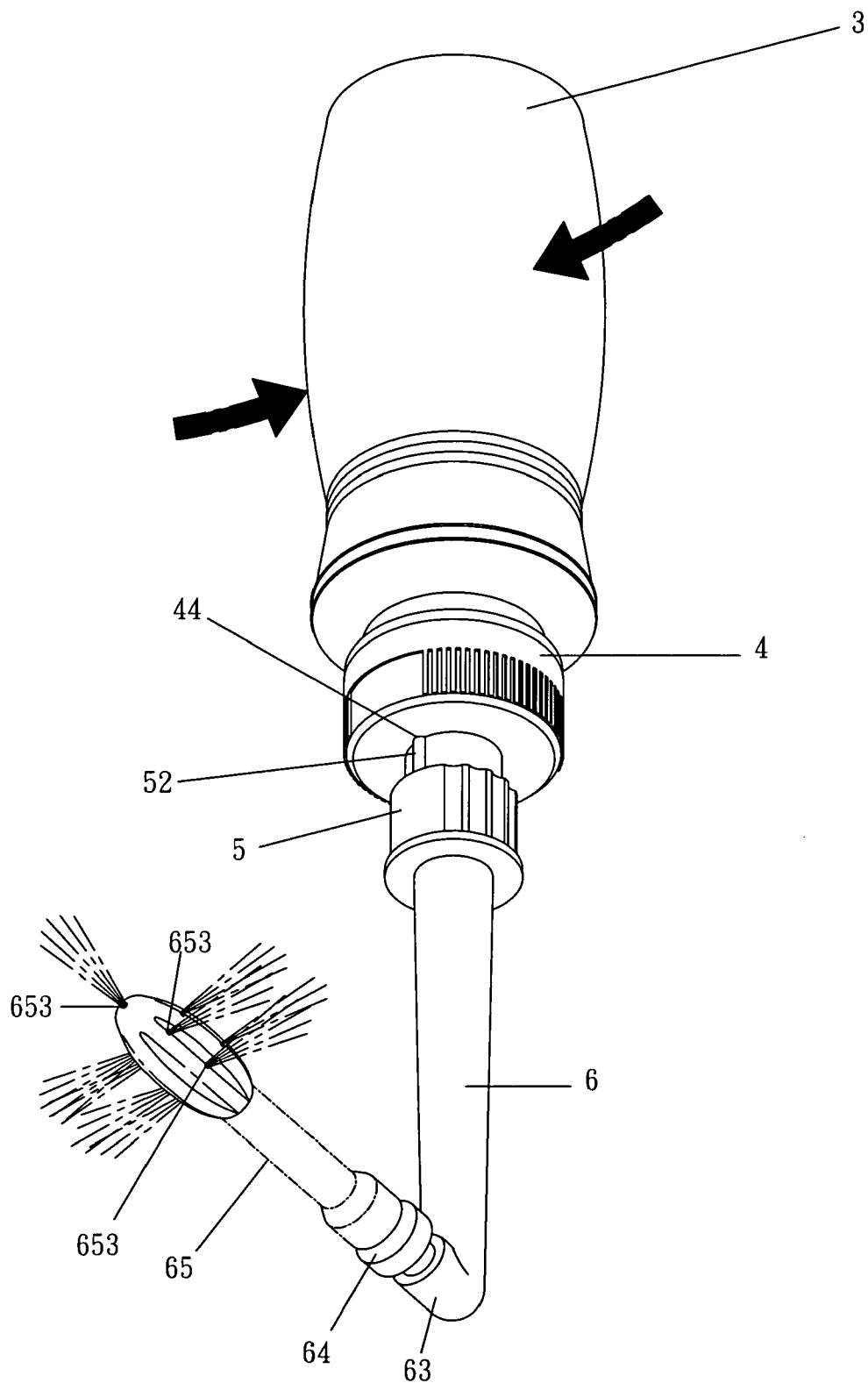
FIG. 8 is a structural schematic view showing operation of the invention

An adjusting cap 5 is internally horizontally made with a separating plate 51 at the middle section thereof, and the separating plate 51 is centrally made with a liquid dispense hole 511 thereon and is made with a positioning ring flange 512 to allow the liquid dispense ring 42 protrudingly made on top surface of the fixing cover 4 to be inserted between the inner bottom section of adjusting cap 5 and positioning ring flange 512, wherein adjusting cap 5 is made with a inserting post 52 at external peripheral edge of the bottom section thereof, and is made with a guide slot 53 at the inner peripheral edge of the bottom section thereof relative to guide post 421 perpendicularly made at external peripheral edge of liquid dispense ring 42 on the top surface of fixing cover 4 so as to allow the bottom end of adjusting cap 5 to sleevedly combine with liquid dispense ring 42 on top surface of fixing cover 4, inserting post 52 at external peripheral edge of bottom section of adjusting cap 5 can be easily alignedly matched with vent hole 44 made on top surface of fixing cover 4 (as shown in FIG. 5-A), and the adjusting cap 5 is made with a threaded section 54 on the peripheral edge of top section thereof and is further internally upwardly made with a positioning ring flange 513 on the top side of separating plate 51 thereof A dispense lever 6 being peripherally made with threaded section 61 at inner edge of bottom section thereof is lockingly engaged with threaded section 54 at the inner peripheral edge of top section of adjusting cap 5, while when bottom section of dispense lever 6 is locking combined with top section of adjusting cap 5, it is through positioning ring flange 513 upwardly made on inner separating plate 51 of adjusting cap 5 to limit the threaded section 61 of bottom section of dispense lever 6 between inner top section of adjusting cap 5 and positioning ring flange 513. The dispense lever 6 is internally made with a hollow flow path 62 having its front end being sidely extended with a branch 63, the rear end of branch 63 is made to appear a globe 631, peripheral edge of globe 631 is sleevedly combined with rear section 641 of a connector 64 being internally made with a through hole 642, while front section of connector 64 is made with threaded section 643 to be lockingly engaged with rear section of a spray head 65, wherein the spray head 65 is internally made with a flow path 652 being interconnected with through hole 642 of connector 64 and is peripherally made with several nozzle holes 653 at the most front end and front end thereof.

A valve device 7 comprises a tube piece 71, ball retainer 72 and a ball 73, wherein top end of tube piece 71 is sleevedly affix to positioning tube 441 being protrudingly made at peripheral edge of vent hole 44 on bottom surface of cover 4, while ball retainer 72 is sleevedly connected to the rear end of tube piece 71, and is internally made with a container 721 from bottom end opening, the bottom end opening is ringly made with several cut slots 722 at peripheral edge thereof, the external peripheral edge of top section of ball retainer 72 is made to a gradual reducing shape 7231 for conveniently insertion into bottom end of tube piece 71, the ball retainer 72 is centrally made with a through hole 723 to be interconnected with container 721 at top end thereof; the ball 73 is inserted into container 721 from bottom end of ball retainer 72, through the functions of several cut slots 722 peripherally made at edge of bottom end of ball retainer 72, when top end of ball retainer 72 is inserted into the inside rear end of tube piece 71, the opening peripheral edge of container 721 is thus elastically compressed to limit ball 73 for sliding inside container 721 of ball retainer 72 with detachment, and the diameter of ball 73 is made slightly larger than the through hole 723 made at the top end of ball retainer 72.

Through the embodiment of above said structures shown in FIGS. 5 to 11, women in their menstruation can carry the device personally on the go, wherein cleansing fluid is first filled in bottle body 3 before use, then rear end 651 of spray head 65 of dispense lever 6 is lockingly engaged with threaded section 643 of connector 64, and bottom section of dispense lever 6 is lockingly combined with top section of adjusting cap 5, liquid dispense ring 42 protrudingly made on top surface of fixing cover 4 is sleevedly inserted to between inner bottom section of adjusting cap 5 and positioning ring flange 512 downwardly made on inner separating plate 51 so as to allow column 43 protrudingly made at center of fixing cover 4 to insert into the liquid dispense hole 511 made at inner middle section of adjusting cap 5, while bottom end of inserting post 52 at external peripheral edge of bottom section of adjusting cap 5 is inserted into vent hole 44 made near to the external peripheral edge of liquid dispense ring 42 on top surface of fixing cover 4, top end of tube piece 71 of valve device 7 is sleevedly affix to the positioning tube 441 protrudingly made at peripheral edge of vent hole 44 on bottom surface of fixing cover 4, and lastly fixing cover 4 and bottle opening 31 of bottle body 3 is lockingly combined to become the portable type hygiene washer (as shown in FIG. 5 and FIG. 5-A) of the present invention.

Figure 9:
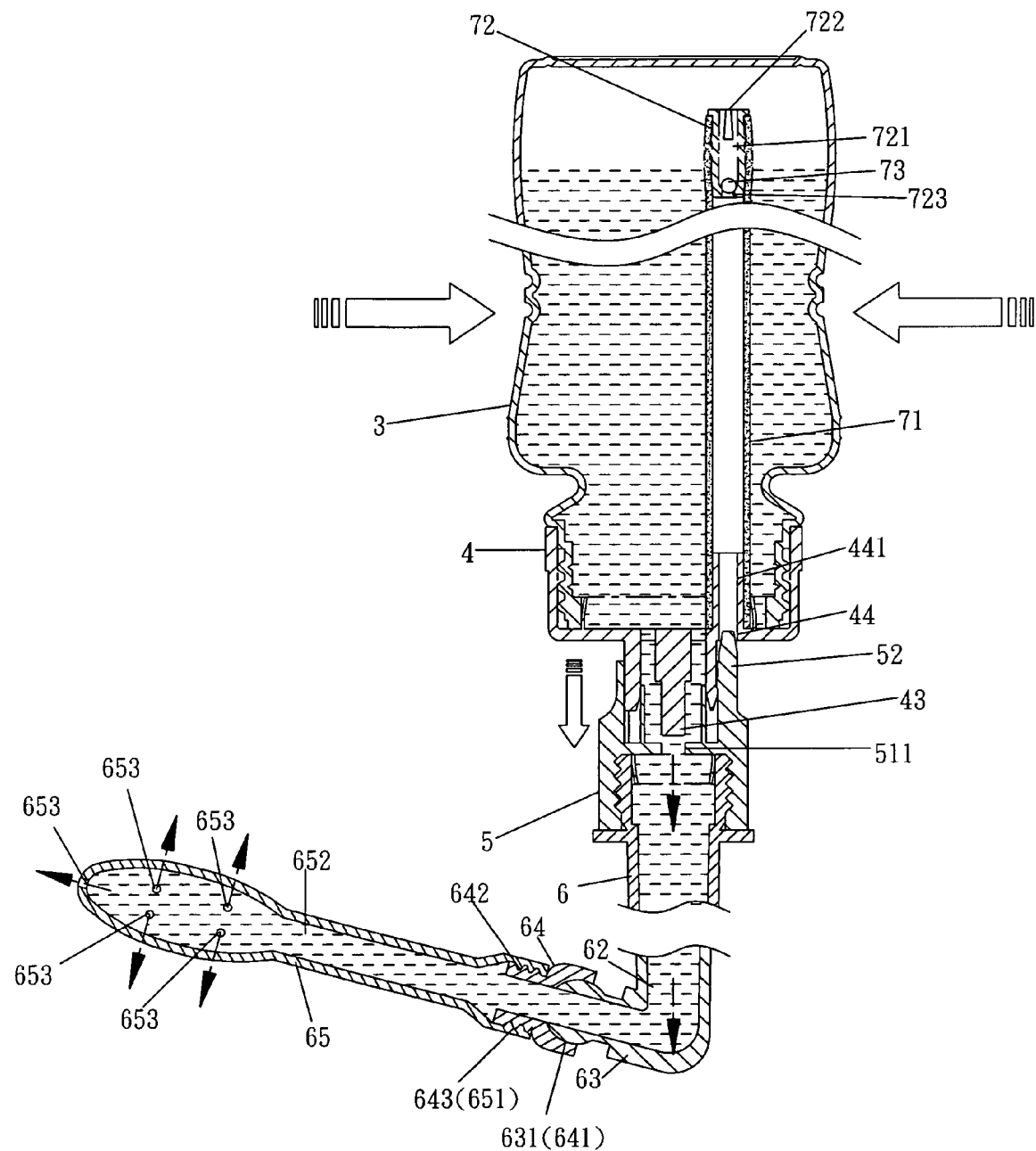
FIG. 9 is a cross-sectional schematic view showing operation of the embodied structure of the invention.

For use, the adjusting cap 5 is pulled upwardly, wherein through the effect of outwardly expanded flange 422 made at external peripheral edge of top end of liquid dispense ring 432 on the top surface of fixing cover 4, the adjusting cap 5 is not detached away from fixing cover 4, but front end of column 43 being protrudingly made at center of fixing cover 4 is made to detach away from liquid dispense hole 511 at inner middle section of adjusting cap 5 thereby forming a flow circuit status, and bottom end of inserting post 52 at external peripheral edge of bottom section of adjusting cap 5 is also detached away from vent hole 44 near to external peripheral edge of liquid dispense ring 42 on top surface of fixing cover 4 thereby forming a flow circuit, further, the hygiene washer is held upside down, wherein the design of globe 631 at rear end of branch 63 being sidely extended at front end of dispense lever 6, the connector 64 being sleevedly combined with globe 631 is rotationally adjusted within certain angles, spray head 65 attached to front end of connector 64 can also be relatively adjusted within certain angles to allow front section of spray head 65 to be matchingly adjusted according to woman's vagina angle thus providing a more convenient way to align and insert into the vagina; then, bottle body 3 is pressed (as shown in FIG. 9, FIG. 9-A), ball 73 contained inside ball retainer 72 being sleevedly affixed to bottom end of tube piece 71 is upside down plugged into through hole 723 made at top end of ball retainer 72 and is tightly closed. The cleansing fluid is flowed from bottle opening 31 of bottle body 3 through the space between liquid dispense ring 42 protrudingly made on top surface of fixing cover 4, further through liquid dispense hole 511 made on inner middle section separating plate 51 of adjusting cap 5 and the inner flow path 61 of dispense lever 6, and is finally sprayed out from nozzle openings 653 ringly made at front end of dispense lever 6 thereby to cleanse the vagina and pudendum, wherein since the bottle body 3 of hygiene washer is used upside down during the process and spray head 65 at front end of dispense lever 6 being alignignly inserted into vagina is below bottle body 3, soiling solution carrying menstruous blood after spraying wash following spray head 63 is not contact with the hands to provide convenient operation and hygiene effect.

Figure 10:
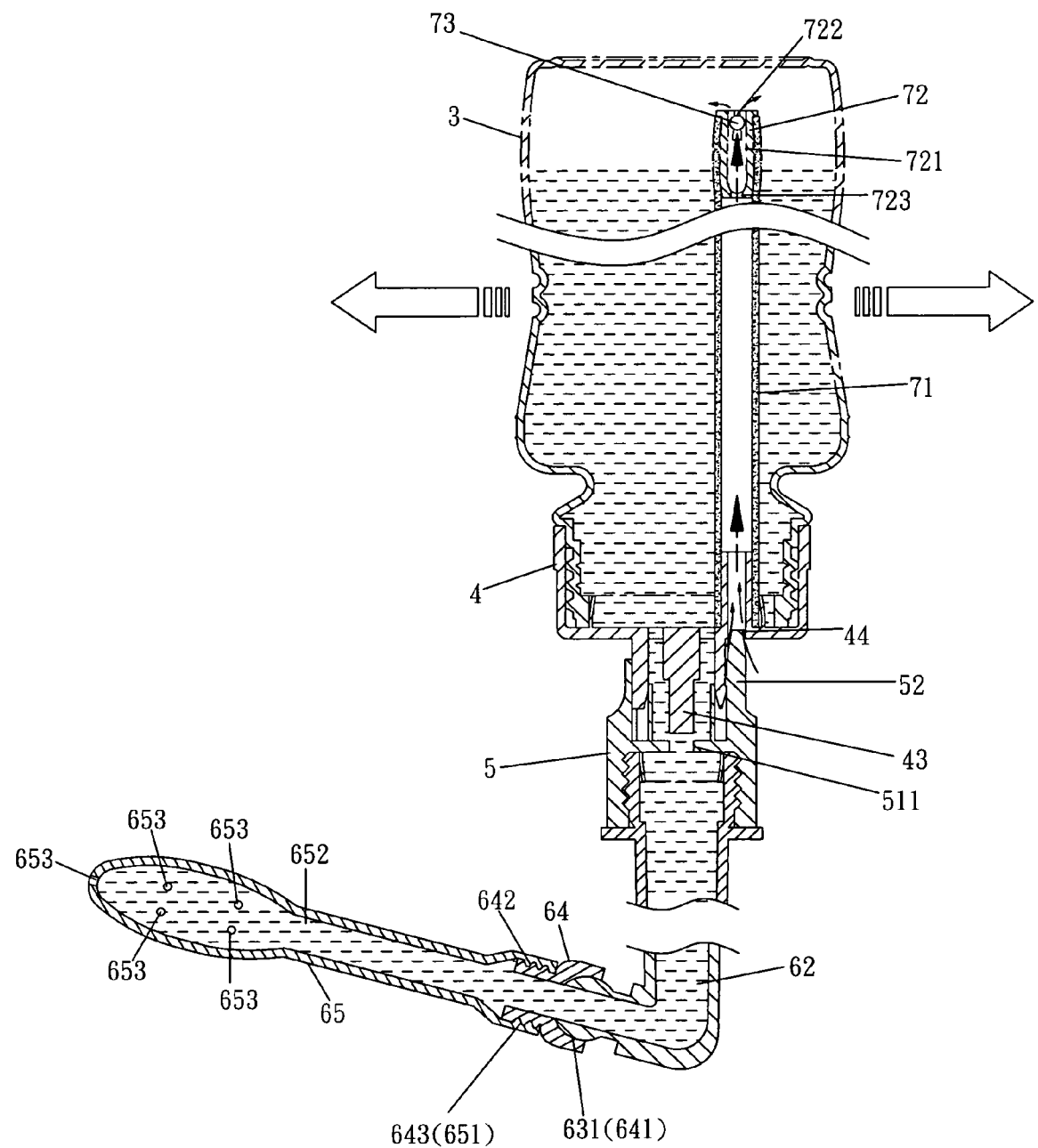
FIG. 10 is a cross-sectional schematic view showing operation of the embodied structure of the invention.
Figure 11:
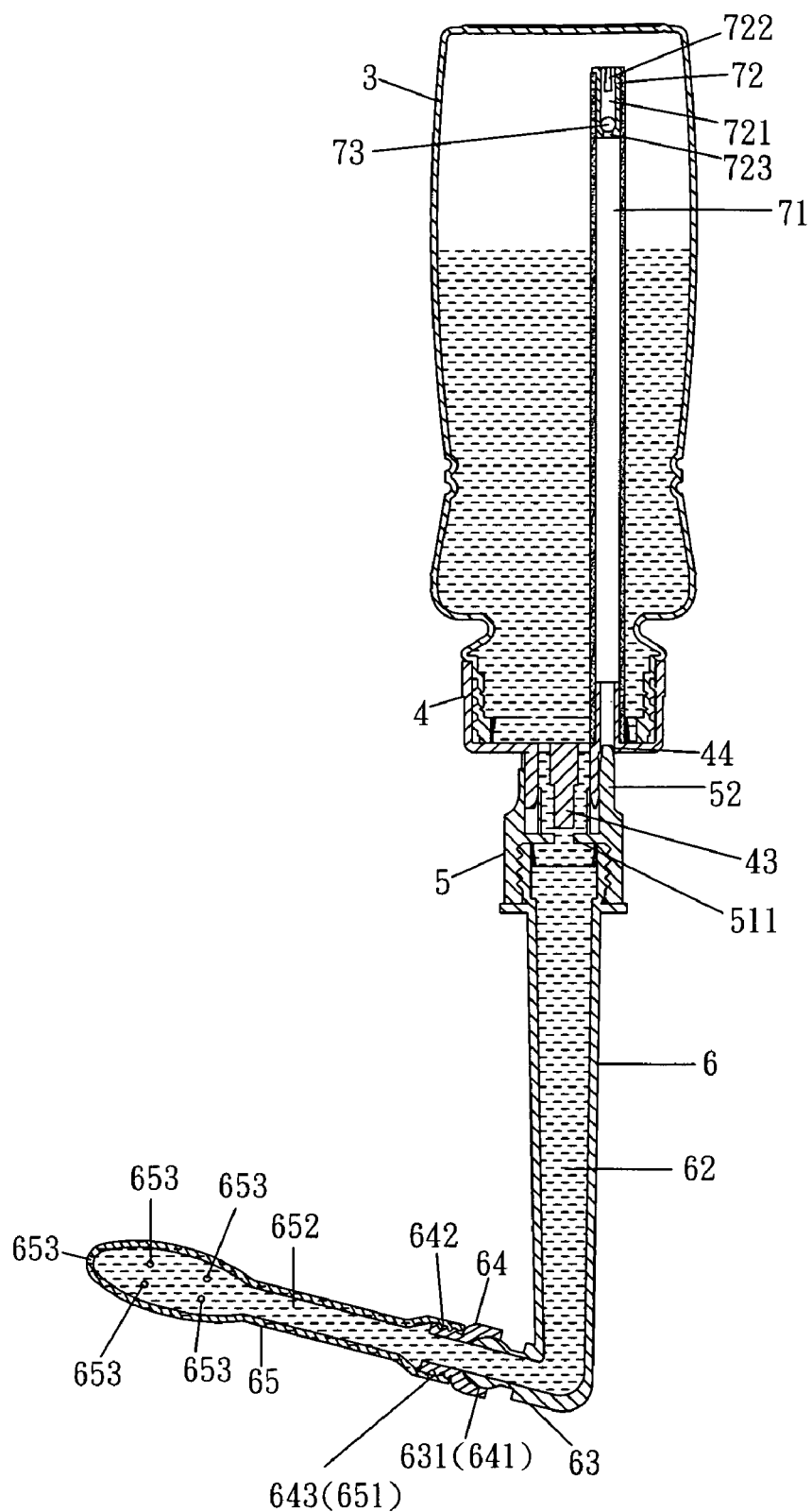
FIG. 11 is a cross-sectional schematic view of the embodied structure of the invention.

When bottle body 3 is pressed by user to allow cleansing fluid to be sprayed out from nozzle holes 653 made at most front end and front section of spray head 65 of dispense lever 6, the bottle body 3 is slightly released simultaneously thereby allowing bottle body in compression to be recovered back to its original shape, wherein air is influenced by the outward tension of bottle body (as shown in FIG. 10 and FIG. 10-A) to enter the flow circuit formed by bottom end of inserting post 52 at external peripheral edge of bottom section of adjusting cap 5 to appear detachment away from vent hole 44 near to external peripheral edge of liquid dispense ring 42 on top surface of fixing cover 4, and pass through inside tube piece 71 of valve device 7 to push ball 73 originally plugged in the through hole 723 on top end of ball retainer 72 upwardly to enter inner top end of bottle body 3 in upside down position through cut slots 722 ringly made at bottom end of ball retainer 72 thereby allowing bottle body 3 to recover back to normal status again (as shown in FIG. 11), and preparing for user to press bottle body 3 again; after that the similar operation is repeated thus achieving the convenience effect to gradually spray out cleansing fluid inside bottle body 3.

Figure 2:
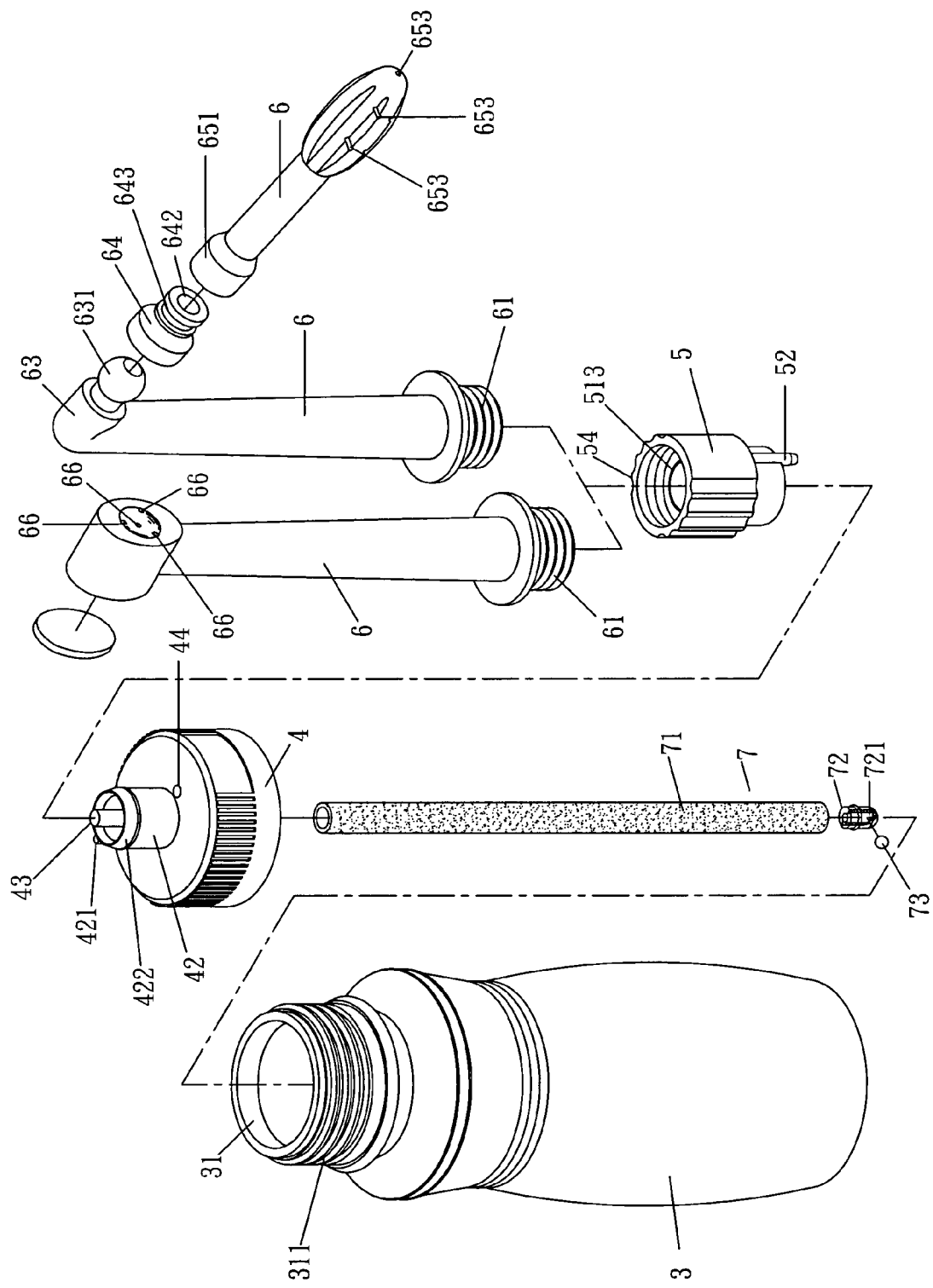
FIG. 2 is a perspective decomposition schematic view of the invented structure.
Figure 3:
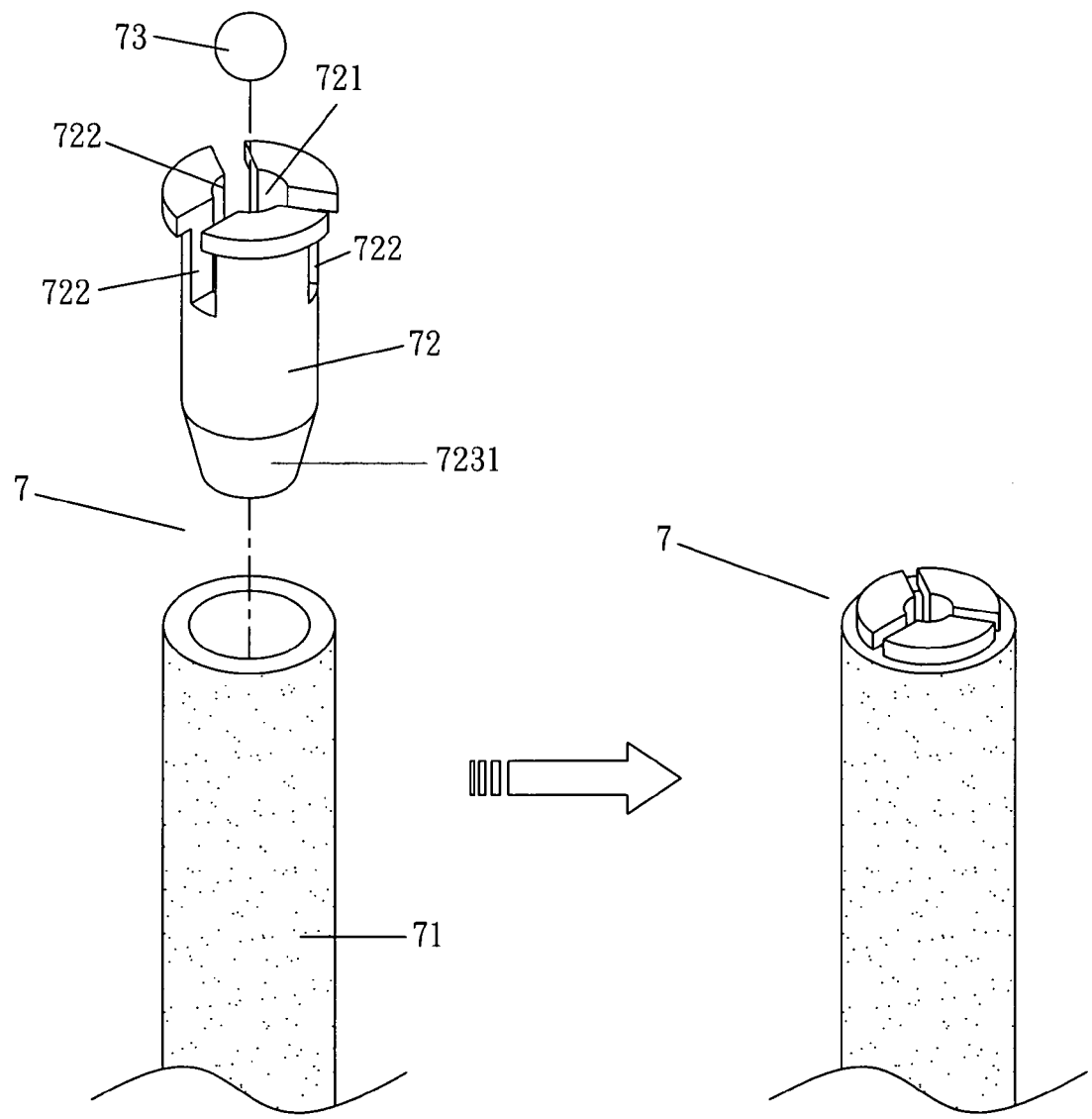
FIG. 3 is a perspective decomposition schematic view showing tube piece, ball retainer and ball in the valve device structure of the invention (placed upside down).
Figure 4:
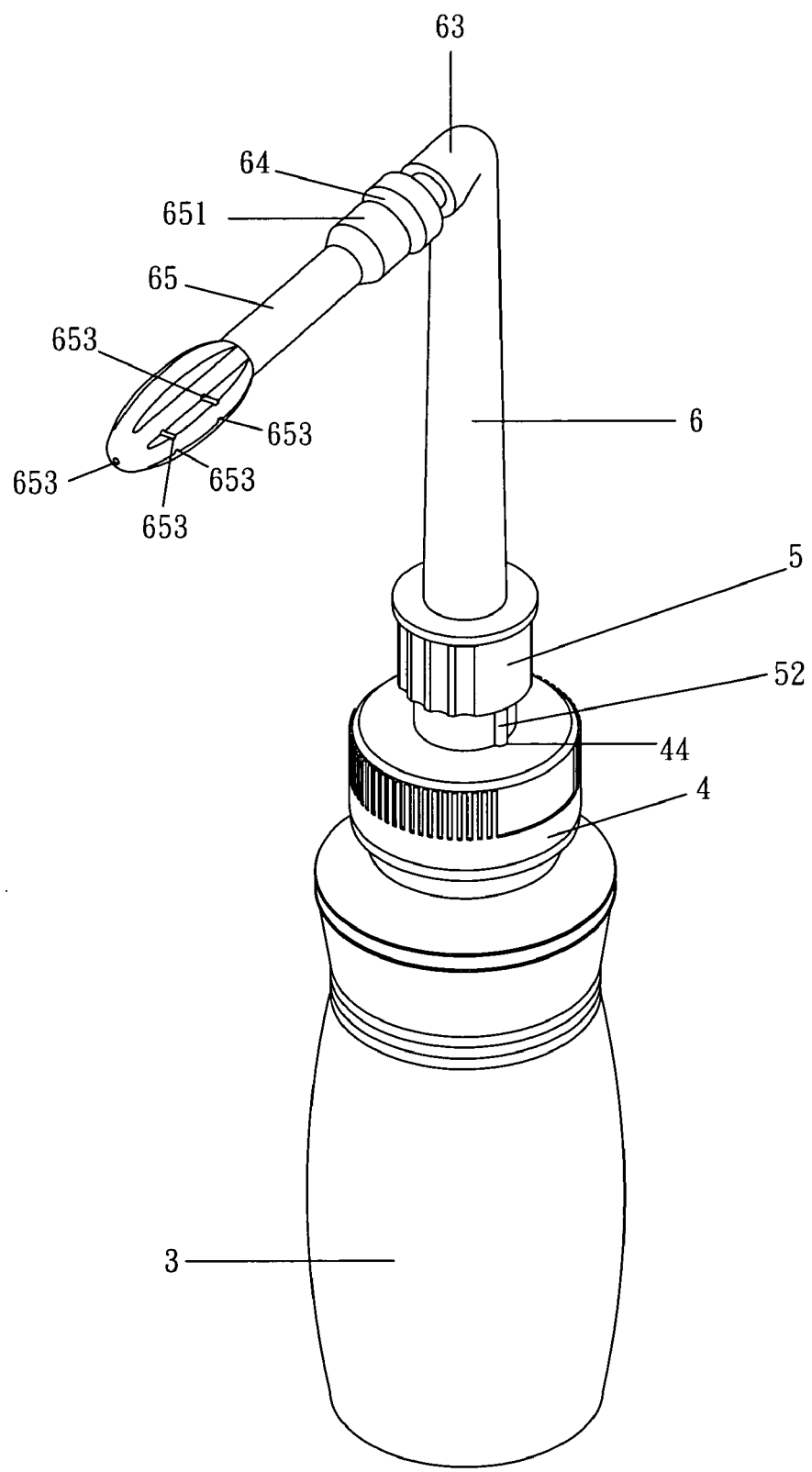
FIG. 4 is a perspective outlook schematic view of the invented structure.
Figure 12:
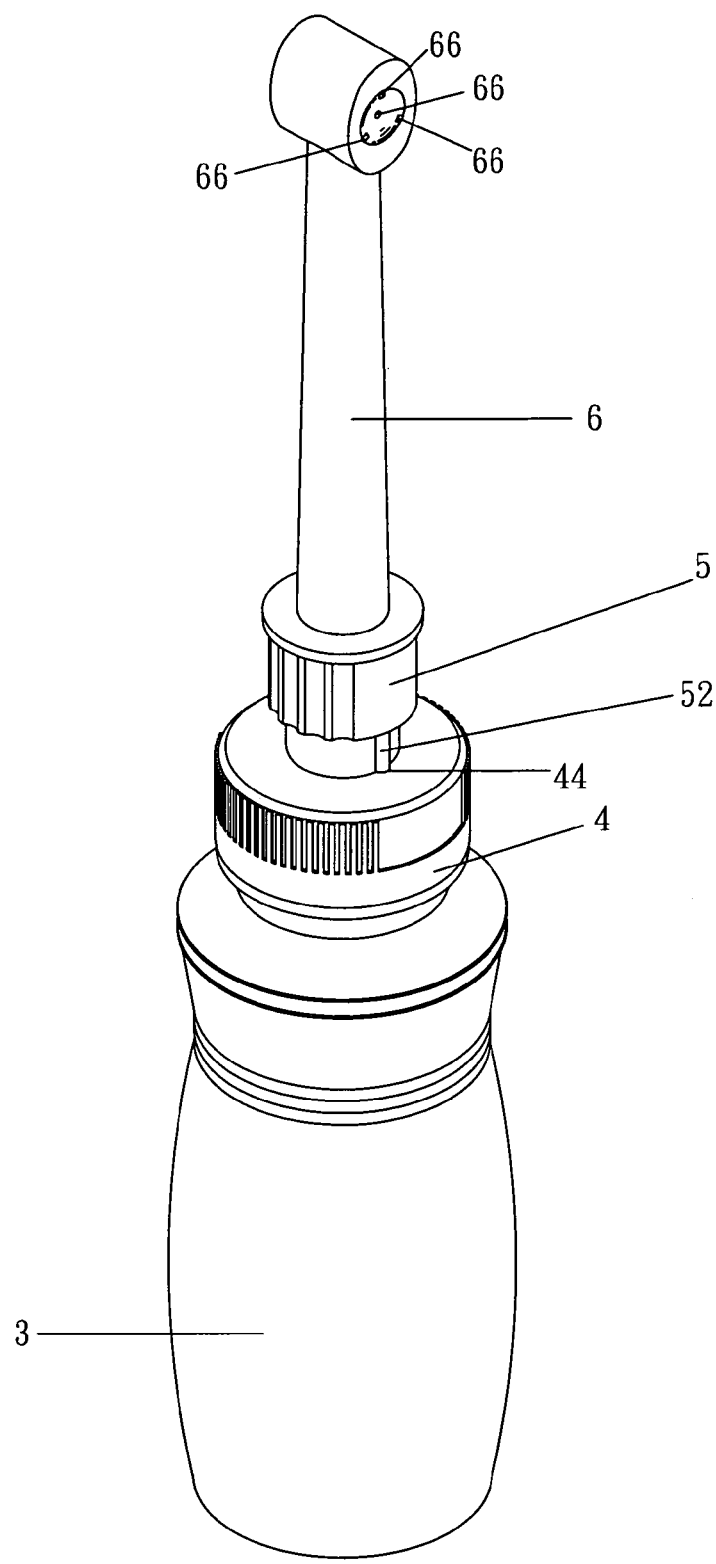
FIG. 12 is a perspective outlook schematic view showing the invention is changed to comprise another embodiment of dispense lever.
Figure 13:
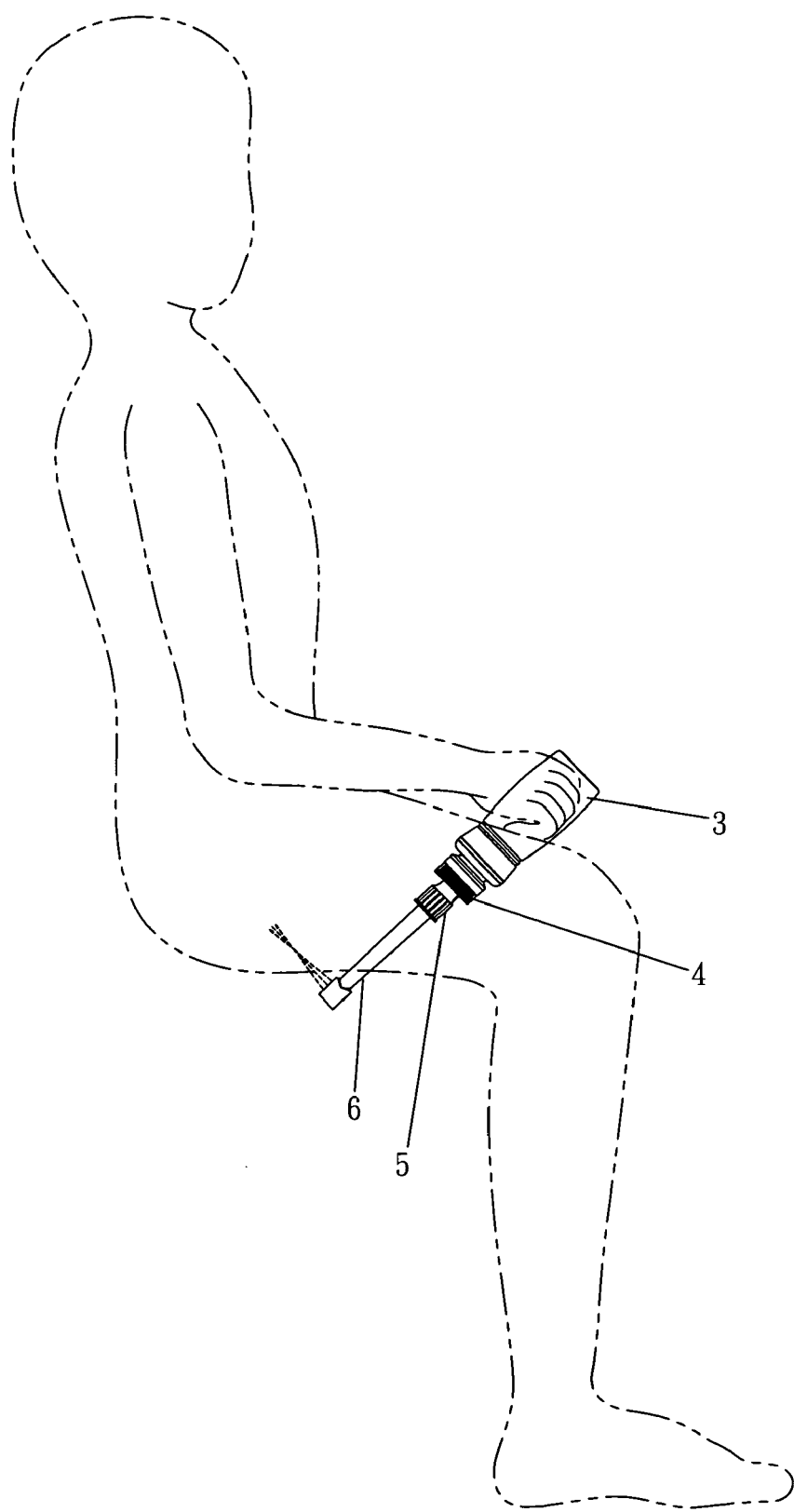
FIG. 13 is a schematic view showing operation of the invention being changed to comprise another embodiment of dispense lever.

Further, as shown in FIG. 2, FIG. 12 and FIG. 13, the dispense lever 6 can also be made with a hollow flow path 62 in the interior thereof and sidely extended to have a branch 63 with its external surface being made to a close shape at one end thereof, wherein several nozzle holes 66 being made on the external side surface is interconnected with the flow path 62, so that a portable type hygiene washer comprising dispense lever 6, bottle body 3, fixing cover 4 and valve device 7 can be provided to allow people after toilet use to thoroughly wash their anal areas thereby achieving convenience effects of better cleanness and hygiene.

I claim:

1. A portable type hygiene washer comprises:
   a bottle body has a bottle opening is peripherally made with threaded section;
   a fixing cover being made with threaded section being lockingly combined with the top bottle opening of bottle body is protrudingly made with a liquid dispense ring, wherein the liquid dispense ring is perpendicularly made with a guide post and is made with an outwardly expanded flange at external ring edge of the top end thereof, the fixing cover is protrudingly centrally made with a column on top surface thereof, the column is peripherally interconnected with the inner edge of the liquid dispense ring through several linking ribs, and the cover is made with a vent hole thereon near to the external peripheral edge of the liquid dispense ring, and a positioning tube is protrudingly made at peripheral edge of the vent hole at the bottom surface thereof;
   an adjusting cap is internally horizontally made with a separating plate at the middle section thereof, and the separating plate is centrally made with a liquid dispense hole thereon and is made with a positioning ring flange to allow the liquid dispense ring protrudingly made on top surface of the fixing cover to be inserted between the inner bottom section of adjusting cap and positioning ring flange, wherein adjusting cap is made with a inserting post at external peripheral edge of the bottom section thereof and is made with a guide slot at external peripheral edge of the bottom section thereof, and is made with threaded section at the peripheral edge of top section of the adjusting cap;
   a dispense lever being peripherally made with threaded section at inner edge of bottom section thereof is lockingly engaged with threaded section at the inner peripheral edge of top section of adjusting cap, and is internally made with a hollow flow path having its front end being sidely extended with a branch, the rear end of branch is made to appear a globe, peripheral edge of globe is sleevedly combined with rear section of a connector being internally made with a through hole, while front section of connector is made with threaded section to be lockingly engaged with rear section of a spray head, wherein the spray head is internally made with a flow path being interconnected with through hole of connector and is peripherally made with several nozzle holes at the most front end and front end thereof;
   a valve device comprises a tube piece, ball retainer and a ball, wherein top end of tube piece is sleevedly affix to positioning tube being protrudingly made at peripheral edge of vent hole on bottom surface of cover, while ball retainer is sleevedly connected to the rear end of tube piece, and is internally made with a container from bottom end opening, the bottom end opening is ringly made with several cut slots at peripheral edge thereof, the ball retainer is centrally made with a through hole interconnected with container at top end thereof; while the ball is inserted into container from bottom end of ball retainer, and the diameter of ball is made slightly larger than the through hole made at the top end of ball retainer,
   wherein the adjusting cap is configured so that the vent hole is blocked by the inserting post of the adjusting cap when in a non-use state and when adjusted to be in a use state the adjusting cap is pulled away from the fixing cover to thereby shift the inserting post to be at least partially removed from the vent hole to temporarily allow air flow through the vent hole.

2. The portable type hygiene washer as claimed in claim 1, wherein the dispense lever can also be made with a hollow flow path in the interior thereof and sidely extended to have a branch with its external surface being made to a close shape at one end thereof, wherein several nozzle holes being made on the external side surface is interconnected with the flow path, so that a portable type hygiene washer comprising dispense lever, bottle body, fixing cover and valve device can be provided to allow people after toilet use to thoroughly wash their anal areas thereby achieving convenience effects of better cleanness and hygiene.

3. The portable type hygiene washer as claimed in claim 1, the bottle body can be made of compressible material.

4. The portable type hygiene washer as claimed in claim 1, wherein liquid dispense ring protrudingly made on top surface of fixing cover is perpendicularly made with a guide post at external peripheral edge thereof and is made with a guide slot at the inner peripheral edge of the bottom section thereof, and guide post and guide slot are alignedly matched.

5. The portable type hygiene washer as claimed in claim 1, wherein the separating plate at internal middle section of adjusting cap can be made with a positioning ring flange on top side thereof.

6. The portable type hygiene washer as claimed in claim 1, wherein external peripheral edge of top section of ball retainer can be made to a gradual reducing type.

* * * * *